United States Patent
Robinson et al.

(10) Patent No.: US 12,162,847 B2
(45) Date of Patent: Dec. 10, 2024

(54) LUMINESCENT COMPOUNDS

(71) Applicant: CHROMATWIST LIMITED, Birmingham (GB)

(72) Inventors: Alex Robinson, Birmingham (GB); Jon Andrew Preece, Birmingham (GB); Gregory O'Callaghan, Birmingham (GB); Karolis Virzbickas, Birmingham (GB); Owen Jones, Birmingham (GB); Dennis Zhao, Birmingham (GB); Michael Butlin, Birmingham (GB); Sareena Sund, Birmingham (GB)

(73) Assignee: CHROMATWIST LIMITED, Birmingham (GB)

( * ) Notice: Subject to any disclaimer, the term of this patent is extended or adjusted under 35 U.S.C. 154(b) by 832 days.

(21) Appl. No.: 16/982,952

(22) PCT Filed: Mar. 21, 2019

(86) PCT No.: PCT/GB2019/050806
§ 371 (c)(1),
(2) Date: Sep. 21, 2020

(87) PCT Pub. No.: WO2019/180444
PCT Pub. Date: Sep. 26, 2019

(65) Prior Publication Data
US 2021/0070720 A1    Mar. 11, 2021

(30) Foreign Application Priority Data
Mar. 21, 2018 (GB) ................................... 1804512

(51) Int. Cl.
*C07D 277/60* (2006.01)
*C07D 277/68* (2006.01)
(Continued)

(52) U.S. Cl.
CPC ......... *C07D 277/60* (2013.01); *C07D 277/68* (2013.01); *H10K 85/654* (2023.02);
(Continued)

(58) Field of Classification Search
None
See application file for complete search history.

(56) References Cited

U.S. PATENT DOCUMENTS

| 5,766,779 A | * | 6/1998 | Shi .......................... H10K 50/11 313/506 |
| 2002/0070662 A1 | | 6/2002 | Moriyama et al. |

(Continued)

FOREIGN PATENT DOCUMENTS

| CN | 101967147 | 2/2011 |
| CN | 105503897 | 4/2016 |

(Continued)

OTHER PUBLICATIONS

TomovićŽ, . (2004). New discotic liquid crystals based on large polycyclic aromatic hydrocarbons as materials for molecular electronics (Doctoral dissertation, Mainz, Univ., Diss., 2005). (Year: 2004).*

(Continued)

*Primary Examiner* — Dawn L Garrett
(74) *Attorney, Agent, or Firm* — Nixon & Vanderhye PC

(57) ABSTRACT

Polycyclic aromatic hydrocarbons represented by the following general formula (I) wherein X is one of nitrogen, phosphorus, arsenic, antimony, bismuth, sulphur, selenium, tellurium; R independently represents an aromatic group and/or an aliphatic group; Q is one of a cyclic aliphatic hydrocarbon, a cyclic aromatic hydrocarbon, a polycyclic hydrocarbon, a polycyclic aromatic hydrocarbon, and/or a fused polycyclic aromatic hydrocarbon; wherein the sub- (Continued)

stituents independently comprise one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or anaryl group; p is an integer of 1 to 2; q is an integer of 1 to 4; $Y^1$ and $Y^2$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen 20 atom), a cyano group, a nitro group, an alkyl group and/oranaryl group; and x is an integer of 0, 1, 2, 3, 4, 5, 6, 7, 8, 9, 10 or more.

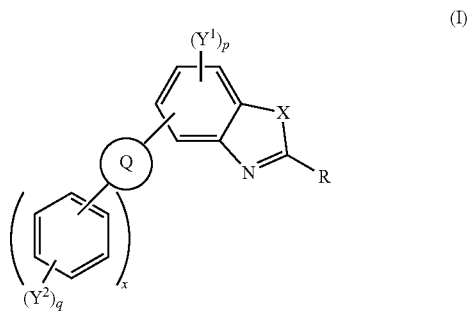

(I)

17 Claims, 5 Drawing Sheets

(51) Int. Cl.
   *H10K 50/11* (2023.01)
   *H10K 85/60* (2023.01)
(52) U.S. Cl.
   CPC ......... *H10K 85/656* (2023.02); *H10K 85/657* (2023.02); *H10K 50/11* (2023.02)

(56) References Cited

U.S. PATENT DOCUMENTS

| | | | |
|---|---|---|---|
| 2003/0171412 | A1 | 9/2003 | Malamas et al. |
| 2004/0076853 | A1* | 4/2004 | Jarikov ................. C09K 11/06 428/917 |
| 2008/0220285 | A1* | 9/2008 | Vestweber ............. C07C 13/72 564/426 |
| 2014/0047976 | A1* | 2/2014 | Yeong .................... B01D 71/64 96/10 |
| 2016/0322569 | A1 | 11/2016 | Yen |
| 2018/0040829 | A1* | 2/2018 | Lee ........................ H10K 99/00 |
| 2019/0355916 | A1* | 11/2019 | Ise ......................... C09B 57/001 |

FOREIGN PATENT DOCUMENTS

| | | |
|---|---|---|
| CN | 105713003 | 6/2016 |
| CN | 108137572 | 6/2018 |
| DE | 10 2016 010 081 | 2/2018 |
| EP | 0 847 228 | 6/1998 |
| GB | 955961 | 4/1964 |
| JP | 2013-071922 | 4/2013 |
| WO | 95/25710 | 9/1995 |

OTHER PUBLICATIONS

Stopel, M. H., Blum, C., & Subramaniam, V. (2014). Excitation spectra and Stokes shift measurements of single organic dyes at room temperature. The Journal of Physical Chemistry Letters, 5(18), 3259-3264. (Year: 2014).*
Chen, Fengkun, et al. "Triphenyleno [1, 2-c: 7, 8-c'] bis ([1, 2, 5] thiadiazole) as a V-Shaped Electron-Deficient Unit to Construct Wide-Bandgap Amorphous Polymers for Efficient Organic Solar Cells." ACS Applied Materials & Interfaces 13.48 (2021): 57743-57749. (Year: 2021).*
Kumar et al., "Novel triphenylenoimidazole discotic liquid crystals", Tetrahedron Letters, Elsevier, Aug. 7, 2011, vol. 52, No. 41, pp. 5363-5367.
Downer et al., "Synthesis of benzothiazoles viaipso substitution of ortho-methoxythiobenzamides", Organic & Biomolecular Chemistry, Jan. 1, 2004, vol. 2, No. 20, p. 3039.
Database PubChem Compound, Dec. 24, 2015, XP002791093, 4 pages.
Haydon et al., "Creating an Antibacterial with in Vivo Efficacy: Synthesis and Characterization of Potent Inhibitors of Bacterial Cell Division Protein FtsZ with Improved Pharmaceutical Properties", Journal of Medicinal Chmistry, May 27, 2019, vol. 53, No. 10, pp. 3927-3936.
Exam Report issued on Jun. 15, 2022 in corresponding European Application 19714751.5, 8 pages.
GB Search Report for GB1804512.0, dated Nov. 6, 2018, 7 pages.
International Search Report and Written Opinion of the ISA for PCT/GB2019/050806 mailed May 24, 2019, 16 pages.
Database PubChem Compound, Dec. 24, 2015, XP002791093.
Jan Najbar et al., "External Heavy Atom Effect On Decay of the Triplet State of Aromatic Hydrocarbons. II. the Decay Functions of Phosphorescence Andof ESR Signals of Triphenylene in the Presence of Iodide Ions," Journal of Luminescence, vol. 11, Issues 3-4, Dec. 1975-Feb. 1976, pp. 215-226.
Maksim V. Sednev et al., "Fluorescent dyes with large Stokes shifts for super-resolution optical microscopy of biological objects: a review," Methods and Applications in Fluorescence 3, Oct. 22, 2015, 042004, 29 pages.
Jack W. Levell et al., "Fluorescence Enhancement by Symmetry Breaking in a Twisted Triphenylene Derivative," J. Phys. Chem. A, Oct. 1, 2010, 114, pp. 13291-13295.
Minrong Zhu et al., "Blue fluorescent emitters: design tactics and applications in organic light-emitting diodes," Chem. Soc. Rev. 2013, Jun. 21, 42(12), pp. 4963-4976.
Neville Boden et al., "Novel Discotic Liquid Crystals created by Electrophilic Aromatic Substitution," J. Mater. Chem., 1995, 5(12), pp. 2275-2281.
Richard C. Powell, "Singlet Exciton Energy Transfer in Organic Solids," Journal of Luminescence vol. 11, Sep.-Nov. 1975, pp. 1-45.
Mar. 14, 2023 Office Action issued in Chinese Patent Application No. 201980033491.0 (pp. 1-22).

* cited by examiner

LUMINESCENT COMPOUNDS

This application is the U.S. national phase of International Application No. PCT/GB2019/050806 filed Mar. 21, 2019 which designated the U.S. and claims priority to GB Patent Application No. 1804512.0 filed Mar. 21, 2018, the entire contents of each of which are hereby incorporated by reference.

This invention relates generally to organic luminescent compounds. More specifically, although not exclusively, this invention relates to novel luminescent polycyclic aromatic hydrocarbon, e.g. triphenylene, derivatives, methods of synthesising the same, uses of the same, and devices comprising the same.

Luminescent compounds are widely used in industrial and research applications as, for example, dyes, probes, sensors, and in electronic devices. These molecules emit light under external energy excitation from sources such as light and/or electrical current.

In photoluminescence, under light irradiation a luminescent compound will absorb light of a specific wavelength and re-emit light of a different wavelength. The type of photoemission observed depends on the molecular structure of the compound.

The difference between the maximum excitation wavelength and the emission wavelength of a luminescent compound is known as the Stokes shift. For use as dyes, probes and/or sensors in industrial applications, it is advantageous for luminescent compounds to possess a large Stokes shift, often defined as greater than 8000 cm$^{-1}$ i.e. a comparatively large difference between the excitation wavelength and emission wavelength. This is advantageous because it minimises the reabsorption of light from the emission of the molecule.

A drawback of many fluorescent dyes with large Stokes shifts is their relatively low brightness, this being defined as the product of the molar extinction coefficient and fluorescence quantum yield. Additionally, dyes with large Stokes shifts often suffer from poor photostability (Methods Appl. Fluoresc. 3 (2015) 042004).

Organometallic complexes that are luminescent often have a large Stokes shift. However, these contain metal centres, e.g. osmium, ruthenium, iridium, rhenium and so on, which are rare, expensive, the complexes are often difficult to synthesise and often toxic. Luminescent organic molecules are often easier to synthesise, but usually exhibit a Stokes shift of relatively smaller magnitude.

In contrast, in electroluminescence, a luminescent compound will emit light in response to an electric current. One of the main applications for this phenomenon is in electronic devices containing OLEDs (Organic Light Emitting Diodes). The OLED material is a layer of a luminescent organic compound, which is situated between two electrodes, one of which is typically transparent. This technology is used in digital displays in electronic devices such as televisions screens, computer monitors, mobile phones, electroluminescent lighting panels and so on.

It is advantageous for luminescent compounds for use in electroluminescent applications to exhibit high brightness. Brightness is defined as the product of the molar extinction coefficient (E) and fluorescence quantum yield ($\phi$) divided by 1000. Consequently, it is advantageous for luminescent compounds to exhibit a high molar extinction coefficient (E) (defined by the Beer-Lambert law, in which A is absorbance, c is the molar concentration of the luminescent compound, and l is the path length), and also a high quantum yield ($\phi$) as a measure of efficiency.

It is well known that polycyclic aromatic hydrocarbons exhibit luminescent properties. One such class of compound is triphenylene and its derivatives. For example, triphenylene may be functionalised with alkoxy chains appended to the periphery of the molecule. In addition, these derivatives exhibit discotic liquid crystalline (DLC) behaviour (J. Nabar and A. Chodkowska, J. Luminescence, 1975, 11, 215). Discotic liquid crystalline behaviour is characterised in that disc-shaped molecules form stacks or columns in a mesophase, which allows charge transfer through $\pi$ stacking, enabling the material to be electrically semi-conductive in the stacking direction. This DLC behaviour, combined with the luminescent properties, is particularly useful for application in technologies such as electronic devices using OLEDs (Organic Light Emitting Diodes), LEDs (Light Emitting Diodes), and for use in solar cells.

It is also known for luminescent compounds to exhibit photoconductivity, in which compounds exhibit increased electrical conductivity in the presence of light by converting the light energy into current. It is known to utilise compounds with good photoconductivity in devices such as solar cells.

Although many luminescent triphenylene derivatives have been synthesised and characterised (Levell et. al. J. Phys. Chem. A., 2010, 114, 13291, for example), it remains a challenge to provide triphenylene derivatives with the advantageous properties described above, i.e. large Stokes shift, high brightness, high molar extinction coefficient, and high quantum yield. Furthermore, it remains a challenge to provide a range of luminescent compounds that emit wavelengths throughout the visible spectrum. Specifically, blue emitters are a particular challenge to provide (Chem Soc Rev. 2013 Jun. 21; 42(12):4963-76).

Furthermore, it remains a challenge to provide luminescent triphenylene derivatives wherein the absorption and the emission energies can be predicted and tuned by design and synthesis to result in specific and desired visible colours (Methods Appl. Fluoresc. 3 (2015) 042004).

Accordingly, a first aspect of the invention provides polycyclic aromatic hydrocarbon derivatives represented by the following general formula:

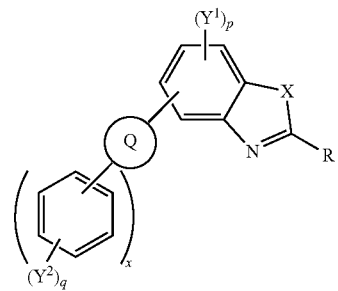

wherein X is one of nitrogen, phosphorus, arsenic, antimony, bismuth, sulphur, selenium, tellurium;

R independently represents an aromatic group and/or an aliphatic group;

Q is one of a cyclic aliphatic hydrocarbon, a cyclic aromatic hydrocarbon, a polycyclic hydrocarbon, a polycyclic aromatic hydrocarbon, and/or a fused polycyclic aromatic hydrocarbon; wherein the substituents independently comprise one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or
an aryl group;
p is an integer of 1 to 2;
q is an integer of 1 to 4;
Y$^1$ and Y$^2$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;
and x is an integer of 0, 1, 2, 3, 4, 5, 6, 7, 8, 9, 10 or more.

In embodiments, Q may represent $C_6H_4$. In embodiments, Q is a polycyclic aromatic hydrocarbon, for example, Q may be one of naphthalene, anthracene, phenanthrene, tetracene, chrysene, triphenylene, pyrene, pentacene, benzo[a]pyrene, corannulene, benzo[ghi]perylene, coronene, ovalene, fullerene, and/or benzo[c]fluorene. Q may be any isomer of the polycyclic aromatic hydrocarbons described, for example, 1-napthalene, 2-napthalene, 2-anthracene, 9-anthracene. The polycyclic aromatic hydrocarbon group may be substituted with other moieties such as aryl groups, alkyl groups, heteroatoms, and/or other electron withdrawing or electron donating groups.

Q is bonded to other six membered rings, e.g. aromatic six membered rings, and/or substituted aromatic six membered rings. The number of six membered rings bonded to Q is represented by the integer x wherein x is 0, 1, 2, 3, 4, 5, 6, 7, 8, 9, 10 or more.

In an embodiment, Q is an aromatic six-membered ring, and x is 2.

In embodiments, the polycyclic aromatic hydrocarbon derivatives may be represented by the following general formula:

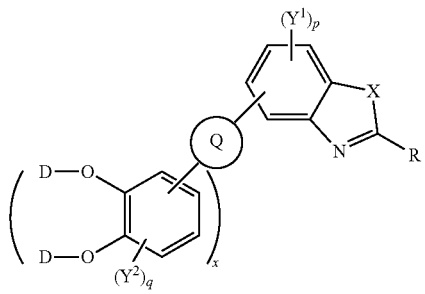

wherein X is one of nitrogen, phosphorus, arsenic, antimony, bismuth, sulphur, selenium, tellurium;
D is a hydrogen atom, a deuterium atom, a silicon atom, or a carbon atom;
p is an integer of 1 to 2;
q is an integer of 1 to 2;
Y$^1$ and Y$^2$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;
and x is an integer of 0, 1, 2, 3, 4, 5, 6, 7, 8, 9, 10 or more.
For example, D may be a linear or branched alkyl chain, an aryl group, or a combination thereof.

The polycyclic aromatic hydrocarbon derivatives may be represented by the following general formula:

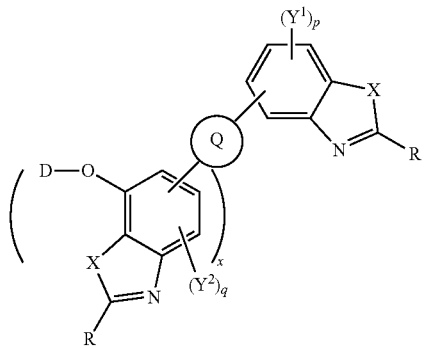

wherein X is one of nitrogen, phosphorus, arsenic, antimony, bismuth, sulphur, selenium, tellurium;
D is a hydrogen atom, a deuterium atom, a silicon atom, or a carbon atom;
p is an integer of 1 to 2;
q is an integer of 1;
Y$^1$ and Y$^2$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;
and x is an integer of 0, 1, 2, 3, 4, 5, 6, 7, 8, 9, 10 or more.
For example, D may be a linear or branched alkyl chain, an aryl group, or a combination thereof.

A further aspect of the invention provides polycyclic aromatic hydrocarbon derivatives, represented by the following general formula:

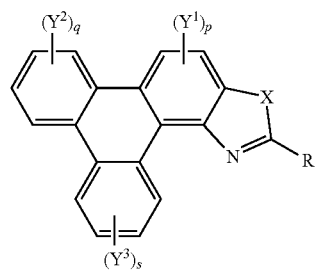

wherein X is one of nitrogen, phosphorus, arsenic, antimony, bismuth, sulphur, selenium or tellurium;
R independently represents an aromatic group and/or an aliphatic group;
p is an integer of 1 to 2;
q and s are independently integers of 1 to 4;
Y$^1$, Y$^2$, and Y$^3$ independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

In embodiments, the polycyclic aromatic hydrocarbon derivative may be a triphenylene derivative. In alternative embodiments, the polycyclic aromatic hydrocarbon derivative may comprise a fused polycyclic aromatic hydrocarbon comprising six 6-membered rings.

$Y^1$, $Y^2$, and $Y^3$ may be one or more of hydrogen atoms, deuterium atoms, oxygen atoms, fluorine atoms, chlorine atoms, carbon atoms, cyano groups, nitro groups carboxylic acid groups, glycol, alkoxy, thioalkoxy, amino, acetate, amide, thioamide, thioester, azo, and/or silyl groups. Additionally or alternatively, $Y^1$, $Y^2$, and $Y^3$ may comprise an alkyl group. The alkyl group(s) may be a straight chain, or may comprise a branched chain, and/or may be further functionalised. Additionally or alternatively, $Y^1$, $Y^2$, and $Y^3$ may comprise an aryl group, The aryl group(s) may be unsubstituted or may be further functionalised. The integer p may be 1 to 2. The integer q may be 1, 2, 3, or 4. The integer s may be 1, 2, 3, or 4.

A yet further aspect of the invention provides polycyclic aromatic hydrocarbon derivatives, represented by the following general formula:

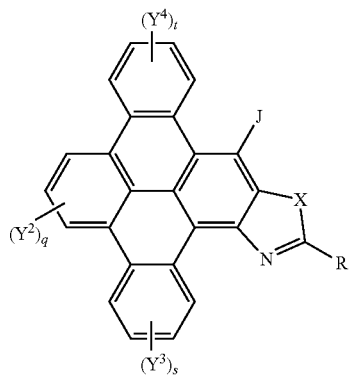

wherein X is one of nitrogen, phosphorus, arsenic, antimony, bismuth, sulphur, selenium or tellurium;
R independently represents an aromatic group and/or an aliphatic group;
q is independently an integer of 1 to 3;
s is independently an integer of 1 to 4;
t is independently an integer of 1 to 4;
$Y^2$, $Y^3$, and $Y^4$ and J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

In embodiments, the polycyclic aromatic hydrocarbon derivatives are triphenylene derivatives, represented by the following general formula:

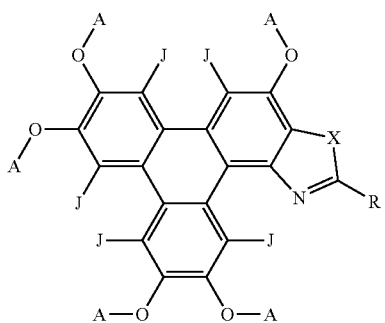

wherein X is one of nitrogen, phosphorus, arsenic, antimony, bismuth, sulphur, selenium or tellurium;
R independently represents an aromatic group and/or an aliphatic group;
A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons) or an alkyl ether;
J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

In embodiments, A may be $C_5H_{11}$ and/or $C_4H_9$. In embodiments, A represents a polyethylene glycol (PEG) group (e.g. $C_2H_4OC_2H_4OC_2H_4OCH_3$.

In embodiments, X is a sulphur atom.

In embodiments, the polycyclic aromatic hydrocarbons are represented by the following general formula:

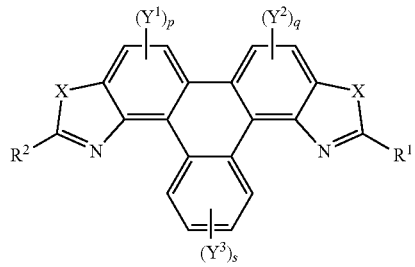

wherein X is independently one of nitrogen, phosphorus, arsenic, antimony, bismuth, sulphur, selenium or tellurium;
$R^1$ and $R^2$ independently represents an aromatic group and/or an aliphatic group;
p and q are independently an integer of 1 to 2;
s is an integer of 1 to 4;
$Y^1$, $Y^2$, and $Y^3$ independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

In embodiments, the polycyclic aromatic hydrocarbons are triphenylene derivatives represented by the following general formula:

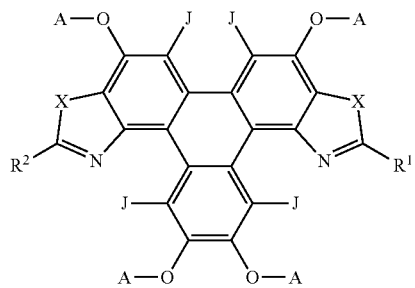

wherein X is independently one of nitrogen, phosphorus, arsenic, antimony, bismuth, sulphur, selenium or tellurium;

$R^1$ and $R^2$ independently represents an aromatic group and/or an aliphatic group;

A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons) or an alkyl ether;

J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

In embodiments, A may be $C_5H_{11}$ and/or $C_4H_9$. In embodiments, A represents a polyethylene glycol (PEG) group (e.g. $C_2H_4OC_2H_4OC_2H_4OCH_3$.

In embodiments, the polycyclic aromatic hydrocarbons are represented by the following general formula:

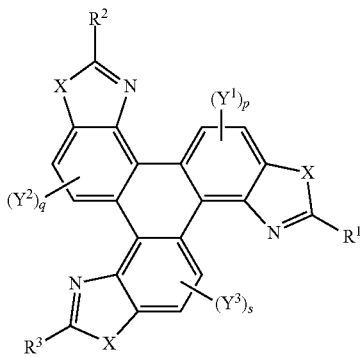

wherein X is independently one of nitrogen, phosphorus, arsenic, antimony, bismuth, sulphur, selenium or tellurium;

$R^1$, $R^2$, $R^3$ independently represent an aromatic group and/or an aliphatic group;

p, q, and s are each independently an integer of 1 to 2;

$Y^1$, $Y^2$, and $Y^3$ independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

In embodiments, the polycyclic aromatic hydrocarbons are triphenylene derivatives represented by the following general formula:

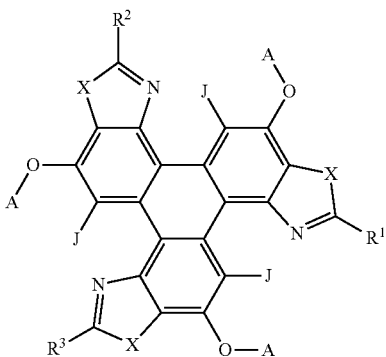

wherein X is independently one of nitrogen, phosphorus, arsenic, antimony, bismuth, sulphur, selenium or tellurium;

$R^1$, $R^2$, $R^3$ independently represent an aromatic group and/or an aliphatic group; A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons) or an alkyl ether;

J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

In embodiments, A comprises further functionality, for example, A may further comprise fluorine atoms, chlorine atoms, cyano groups, nitro groups, glycol, alkoxy, thioalkoxy, polyethylene glycol, amino, acetate, carboxylic acid, amide, thioamide, thioester, azo, and/or silyl groups.

In embodiments, X is a sulphur atom.

In embodiments, J comprises or represents an aryl group, e.g. a phenol group. Additionally or alternatively, J comprises a halogen atom, e.g. fluorine, chlorine, bromine, or iodine.

In embodiments, R, $R^1$, $R^2$, or $R^3$ may be an alkyl group, for example, a straight or branched alkyl chain. In embodiments, at least one of R, $R^1$, $R^2$, $R^3$ may be a methyl, ethyl, propyl, butyl group.

The group R, $R^1$, $R^2$, or $R^3$, may independently be an aromatic group and/or an aliphatic group.

In embodiments wherein R, $R^1$, $R^2$, or $R^3$ is an aromatic group, the aromatic group may be one of, or a combination of, an aromatic hydrocarbon group, and/or an aromatic heterocyclic group.

In embodiments wherein R, $R^1$, $R^2$, or $R^3$ is an aromatic hydrocarbon group, the aromatic hydrocarbon group may comprise one of, or a combination of, a phenyl ring and/or a substituted phenyl ring. There may be one, two, three, four, or five additional substituents on the phenyl ring. The substituents are bonded directly to the phenyl ring, and may be one of, or a combination of, fluorine, chlorine, bromine, iodine, a hydroxyl group, an amine group, a nitro group, an alkoxy group, a carboxylic acid, an amide, a cyano group, a trifluoromethyl, an ester, an alkene an alkyne, an azide, an azo, an isocyanate, a ketone, an aldehyde, an alkyl group consisting of a hydrocarbon chain, or a hydrocarbon ring, an alkyl group consisting of other heteroatoms such as fluorine, chlorine, bromine, iodine, oxygen, nitrogen, and/or sulphur. The alkyl group may comprise a hydroxyl group, an amine group, a nitro group, an ether group, a carboxylic acid, an amide, a cyano group, trifluoromethyl, an ester, an alkene an alkyne, an azide, an azo, an isocyanate, a ketone, an aldehyde, for example. The substituents may be another aromatic group, for example, R may comprise a phenyl substituted with a further phenyl ring. In embodiments, the R group may be a phenyl ring, substituted with a second phenyl ring, which in turn is substituted with a third phenyl ring.

In embodiments wherein R, $R^1$, $R^2$, or $R^3$ is an aromatic group, the aromatic group may be a polycyclic aromatic hydrocarbon, for example, naphthalene, anthracene, phenanthrene, tetracene, chrysene, triphenylene, pyrene, pentacene, benzo[a]pyrene, corannulene, benzo[ghi]perylene, coronene, ovalene, fullerene, and/or benzo[c]fluorene. The R group may be bonded to the polycyclic aromatic hydrocarbon derivative, e.g. the triphenylene derivative, by any isomer of the polycyclic aromatic hydrocarbons described, for example, 1-napthalene, 2-napthalene, 2-anthracene, 9-anthracene. The polycyclic aromatic hydrocarbon group may be substituted with other moieties such as aryl groups, alkyl groups, heteroatoms, and/or other electron withdrawing or electron donating groups.

In embodiments, wherein R, $R^1$, $R^2$, or $R^3$ is an aromatic heterocyclic group, the heterocyclic group may be a three membered ring, a four membered ring, a five membered ring, a six membered ring, a seven membered ring, an eight membered ring, a nine membered ring, a ten membered ring, or a fused ring. In embodiments, the heterocyclic group may be furan, benzofuran, isobenzofuran, pyrrole, indole, isoindole, thiophene, benzothiophene, benzo[c]thiophene, imidazole, benzimidazole, purine, pyrazole, indazole, oxazole, benzoxazole, isoxazole, benzisoxazole, thiazole, benzothiazole, pyridine, quinoline, isoquinoline, pyrazine, quinoxaline, acridine, pyrimidine, quinozoline, pyridazine, cinnoline, phthalazine, 1,2,3-triazine, 1,2,4-triazine, 1,3,5-triazine, pyridine or thiophene.

In embodiments wherein R, $R^1$, $R^2$, or $R^3$ is an aliphatic group, the aliphatic group may be one of, or a combination of, an n-alkyl chain, a branched alkyl chain, an alkyl chain comprising unsaturated moieties, an alkyl chain comprising heteroatoms, for example, fluorine, chlorine, bromine, iodine, oxygen, sulphur, nitrogen. The alkyl chain may comprise unsaturated portions, comprising alkenes, or aromatic moieties. The alkyl chain may comprise functional groups for further derivatisation of the polycyclic aromatic hydrocarbon derivative, e.g. the triphenylene derivative. For example, the functional groups may be one or more of an azide, a carbonyl group, an alcohol, a halogen, or an alkene.

The polycyclic aromatic hydrocarbon, e.g. triphenylene, derivatives may be used, for example, as luminescent dyes for use in devices.

A further aspect of the invention provides a device comprising the polycyclic aromatic hydrocarbon, e.g. triphenylene, derivatives. The device may be an electronic device, for example, an organic electroluminescent device, a thin-film transistor and/or an OPV (organic photovoltaic) device. The electronic device may comprise a digital display, the digital display comprising polycyclic aromatic hydrocarbon, e.g. triphenylene, derivatives of the present invention, for example, a liquid crystal display. The digital display may be in a television screen, a computer monitor, a mobile phone screen, a games console, for example. The organic electroluminescent device may comprise a pair of electrodes and one or more layers interposed therebetween, wherein the one or more layers comprise one or more of the polycyclic aromatic hydrocarbon, e.g. triphenylene, derivatives.

The device may be for the use of detecting species, for example, ions, e.g. metal ions. For example, the polycyclic aromatic hydrocarbon derivative, e.g. the triphenylene derivative, may comprise a moiety that is capable of binding to a species, e.g. an ion. The moiety may be tagged to or integrated into, i.e. covalently bonded to, the polycyclic aromatic hydrocarbon derivative, e.g. the triphenylene derivative. Binding of a species to a polycyclic aromatic hydrocarbon derivative, e.g. a triphenylene derivative, may elicit a luminescent response. The luminescent response may be recorded to quantitatively or qualitatively measure the presence of the species, e.g. in solution. The moiety may be a crown ether, a multidentate ligand, a bidentate ligand or a monodentate ligand. The polycyclic aromatic hydrocarbon, e.g. triphenylene, derivative, e.g. comprising a moiety that is capable of binding to a species, may be spin coated onto a dipstick. The dipstick may comprise a UV LED (light emitting diode). The LED may be illuminated in the presence of specific species upon binding to the polycyclic aromatic hydrocarbon, e.g. triphenylene, derivative, e.g. ions, metal ions. The LED illumination may be specific to a specific species that is bound to the polycyclic aromatic hydrocarbon, e.g. triphenylene, derivative, i.e. a specific wavelength of light, wavelength A, is emitted by the LED upon binding to a specific species, species A, and a different wavelength of light, wavelength B, is emitted by the LED upon binding to a specific species, species B.

The device may be used in biofluorescent microscopy techniques. The device may comprise the polycyclic aromatic hydrocarbon, e.g. triphenylene, derivatives as a luminescent dye that may be used to label biological, or non-biological samples, which may include DNA or proteins or antigens or biomarkers.

The device may comprise a polymer, or a pre-polymer, and/or a resin composition for use in printing, for example, for use in 3D printing plastic products comprising the polycyclic aromatic hydrocarbon, e.g. triphenylene, derivatives. The polycyclic aromatic hydrocarbon, e.g. triphenylene, derivatives may be used as a dopant in the device.

The polycyclic aromatic hydrocarbon, e.g. triphenylene, derivative(s) of the device may emit light in the visible spectrum, i.e. between 380 nm and 750 nm. The triphenylene derivative(s) of the device may exhibit a Stokes shift of between 8000 cm$^{-1}$ to 25,000 cm$^{-1}$, for example, between 15,000 cm$^{-1}$ to 25,000 cm$^{-1}$. The polycyclic aromatic hydrocarbon derivatives, e.g. triphenylene derivative(s), of the device may exhibit a conductivity value of $5.0\times10^{-13}$ S cm$^{-1}$ and $1.5\times10^{-11}$ S cm$^{-1}$, for example, between $6\times10^{-12}$ S cm$^{-1}$ and $1.5\times10^{-11}$ S cm$^{-1}$. The polycyclic aromatic hydrocarbon, e.g. triphenylene, derivative(s) of the device may) exhibit a photoconductivity when irradiated at 350 nm of between $1.5\times10^{-10}$ S cm$^{-1}$ and $1\times10^{-3}$ 5 cm$^{-1}$, for example, between $1\times10^{-8}$ S cm-1 and $1\times10^{-3}$ cm$^{-1}$.

A yet further aspect of the invention provides a method of synthesising polycyclic aromatic hydrocarbons, e.g. triphenylene derivatives, (P1) comprising the general formula:

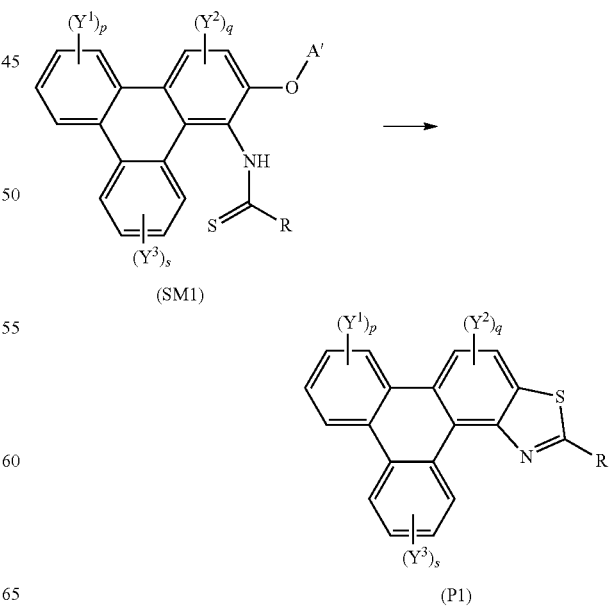

(SM1)

(P1)

wherein R independently represents an aromatic group and/or an aliphatic group;
p is an integer of 1 to 2;
q and s are independently integers of 1 to 4;
$Y^1$, $Y^2$, and $Y^3$ independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

In embodiments, the polycyclic aromatic hydrocarbon derivative may be a triphenylene derivative.

In this embodiment, (SM1) represents a polycyclic aromatic hydrocarbon core and (P1) represents a polycyclic aromatic hydrocarbon derivative. A' may be an alkyl chain, for example, an alkyl chain comprising three or more carbon atoms, e.g. four, five, six, seven, or more carbon atoms. The method may involve the polycyclic aromatic hydrocarbon core (SM1) undergoing an intramolecular rearrangement to produce a polycyclic aromatic hydrocarbon derivative (P1).

A yet further aspect of the invention provides a method of synthesising polycyclic aromatic hydrocarbon derivatives, e.g. triphenylene derivatives, (P2) comprising the general formula:

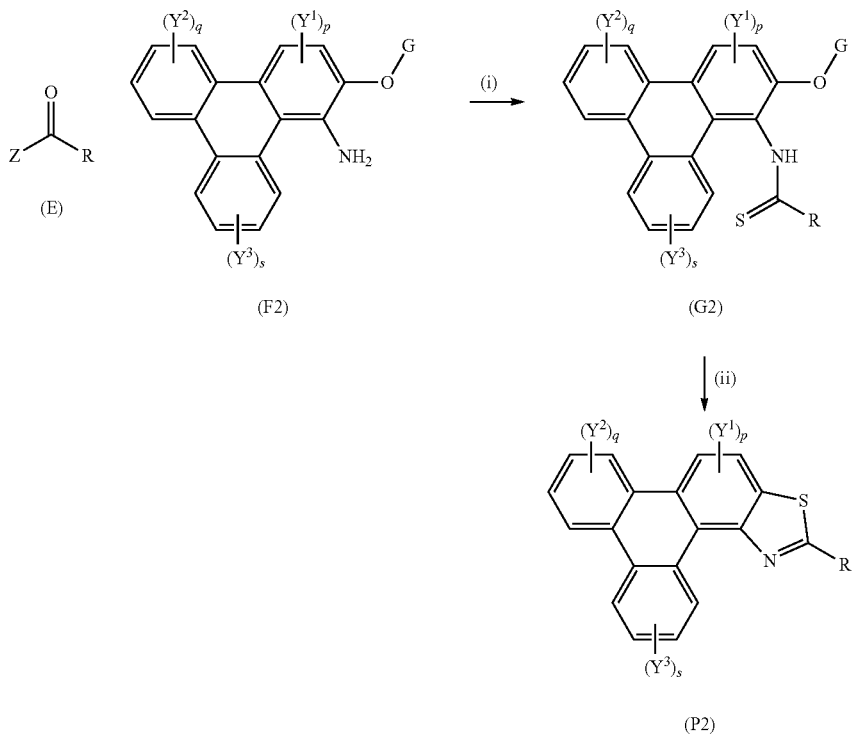

wherein (F2) represents the polycyclic aromatic hydrocarbon starting material, (P2) represents the polycyclic aromatic hydrocarbon derivative;
G is a carbon atom, e.g. an alkyl chain, or an aryl group;
p is an integer of 1 to 2;
q and s are integers of 1 to 4;
$Y^1$, $Y^2$, and $Y^3$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;
(E) represents the reagent;
R independently represents an aromatic group and/or an aliphatic group;
Z is one of an oxygen atom, a derivatised oxygen atom, a chlorine atom, or a bromine atom, or any good leaving group.

Compound (F2) represents the polycyclic aromatic hydrocarbon core, wherein group G may be a carbon atom, e.g. an alkyl chain, or an aryl group. (E) represents the reagent, wherein R is an aromatic group and/or an aliphatic group, and group Z may be one of an oxygen atom, a derivatised oxygen atom, e.g. an OH group; a chlorine atom, or a bromine atom, or any good leaving group. Reagent (E) may be an acyl chloride or a carboxylic acid. The method may involve Step (i) the polycyclic aromatic hydrocarbon core (F2) and the reagent (E) undergoing an intermolecular coupling reaction to produce the polycyclic aromatic hydrocarbon intermediate (G2). The polycyclic aromatic hydrocarbon intermediate (G2) may undergo Step (ii) a thionation reaction followed by an intramolecular cyclisation reaction to afford the polycyclic aromatic hydrocarbon derivatives (P2).

In embodiments, the polycyclic aromatic hydrocarbon derivative (P2) may be a triphenylene derivative.

Step (ii) of the method may be performed using a thionating agent, for example, Lawesson's reagent, ammonium phosphorodithioate or thiophosphoryl chloride with triethylamine.

The method of synthesising triphenylene derivatives (P3) may comprise the general formula:

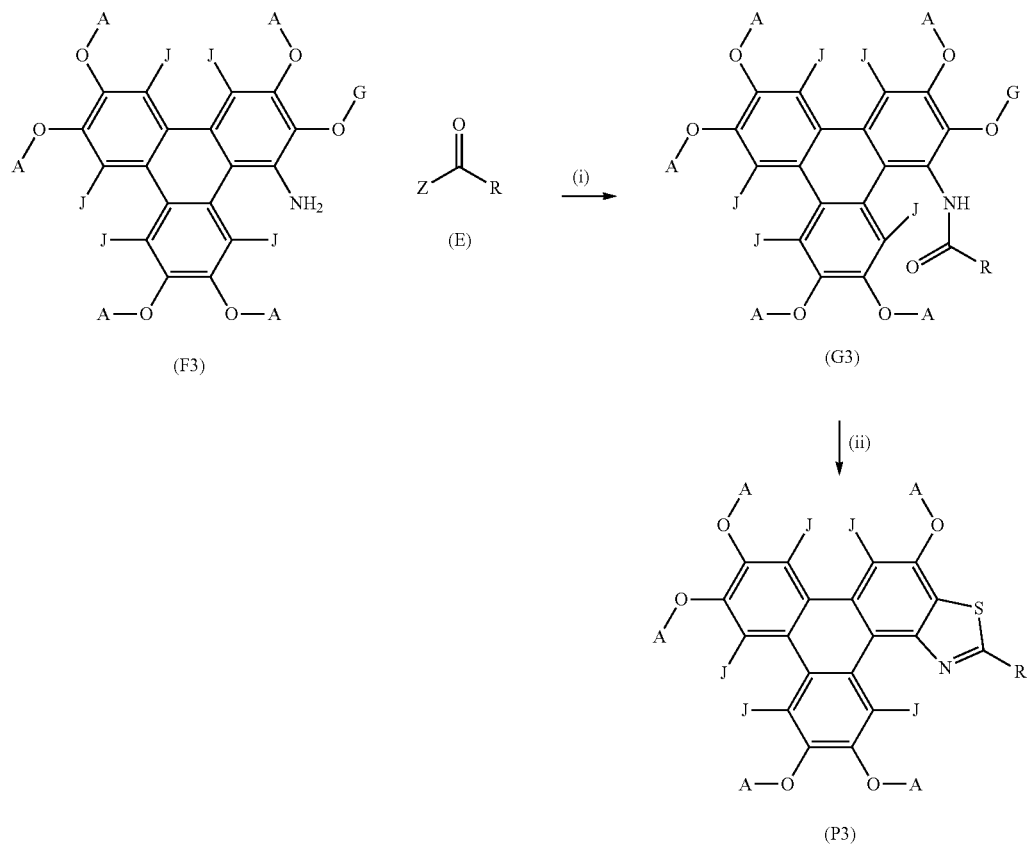

(F3)

(G3)

(P3)

wherein (F3) represents a triphenylene core, (P3) represents a triphenylene derivative;

A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons);

J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

G is a carbon atom;

(E) represents the reagent;

R independently represents an aromatic group and/or an aliphatic group;

Z is one of an oxygen atom, a derivatised oxygen atom, a chlorine atom, or a bromine atom, or any good leaving group.

(F3) represents the triphenylene core, G may be an alkyl or aryl group, (E) represents the reagent, R is an aromatic group and/or an aliphatic group, Z is one of an oxygen atom, e.g. an OH group, a derivatised oxygen atom, a chlorine atom, or a bromine atom, or any good leaving group, and wherein the triphenylene core (F3) and the reagent (E) undergo Step (i) an intermolecular coupling reaction to produce the triphenylene intermediate (G3).

The triphenylene intermediate (G3) may undergo Step (ii) a thionation reaction followed by an intramolecular cyclisation reaction to afford the triphenylene derivatives (P3).

Step (ii) of the method may be performed using a thionating agent, for example, Lawesson's reagent ammonium phosphorodithioate or thiophosphoryl chloride with triethylamine.

For example, the method of synthesising triphenylene derivatives (M) may comprise the formula:

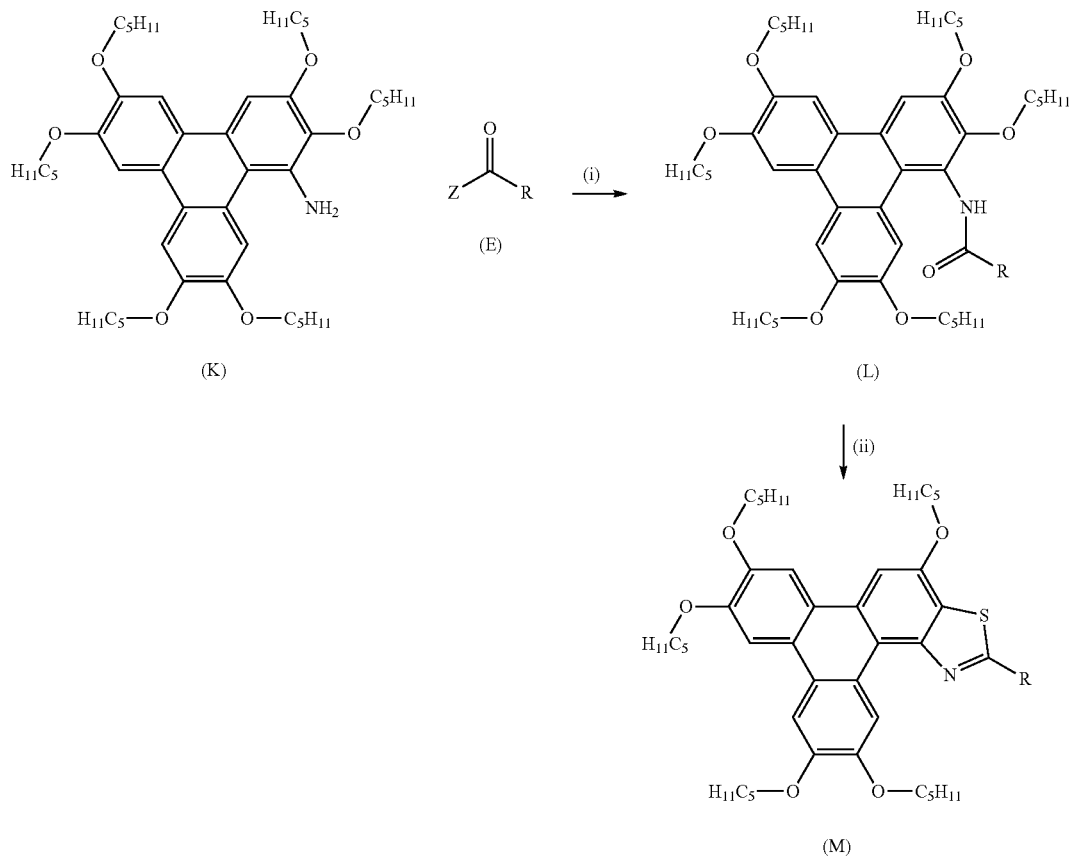

A yet further aspect of the invention provides a method of synthesising polycyclic aromatic hydrocarbons, e.g. triphenylene derivatives, (P4), the method comprising the following general formula:

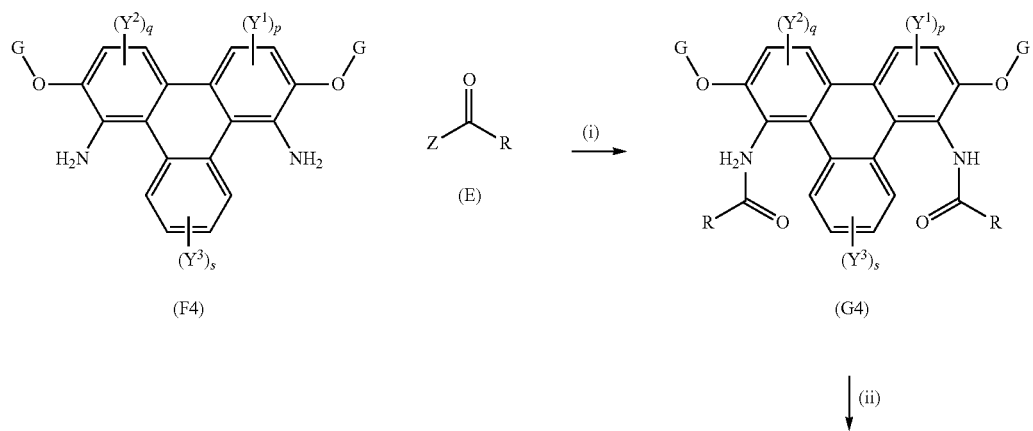

-continued

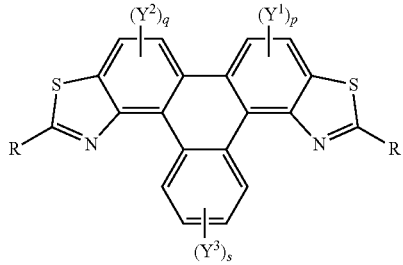

(P4)

wherein (F4) represents a polycyclic aromatic hydrocarbon core, (P4) represents a polycyclic aromatic hydrocarbon derivative;
p is an integer of 1 to 2;
q is an integer of 1 to 2;
s is an integer of 1 to 4;
$Y^1$, $Y^2$, and $Y^3$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;
G independently represents a substituted carbon atom;
(E) represents the reagent; R independently represents an aromatic group and/or an aliphatic group;
Z is one of an oxygen atom, a derivatised oxygen atom, a chlorine atom, or a bromine atom, or any good leaving group.

The method of synthesising triphenylene derivatives (P5) may comprise the general formula:

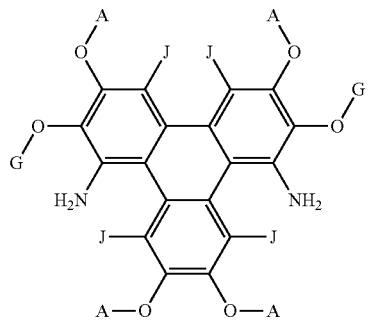  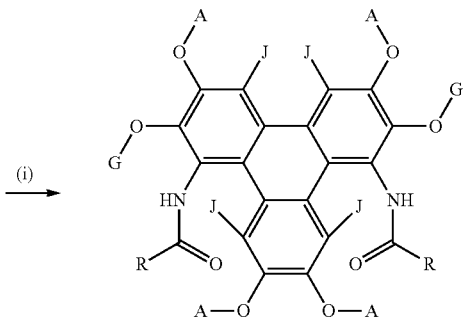

(F5) (E) (G5)

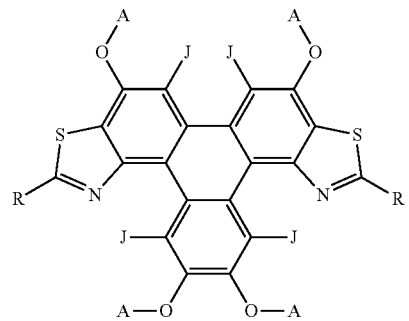

(P5)

wherein (F5) represents a triphenylene core, (P5) represents a triphenylene derivative;

A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons);

J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

G independently represents a substituted carbon atom;

(E) represents the reagent;

R independently represents an aromatic group and/or an aliphatic group;

Z is one of an oxygen atom, a derivatised oxygen atom, a chlorine atom, or a bromine atom;

(F5) represents the triphenylene core, G is an alkyl, hydrogen atom or aryl group, (E) represents the reagent, R is an aromatic group and/or an aliphatic group, Z is one of an oxygen atom, a derivatised oxygen atom, a chlorine atom, or a bromine atom, and wherein the triphenylene core (F5) and the reagent (E) undergo Step (i) an intermolecular coupling reaction to produce the triphenylene intermediate (G5). The triphenylene intermediate (G5) may undergo Step (ii) a thionation reaction followed by an intramolecular cyclisation reaction to afford the triphenylene derivatives (P5).

Step (ii) of the method may be performed using a thionating agent, for example, Lawesson's reagent ammonium phosphorodithioate or thiophosphoryl chloride with triethylamine.

The triphenylene core (F5) of the method of synthesising triphenylene derivatives (P5) may comprise the formula (N):

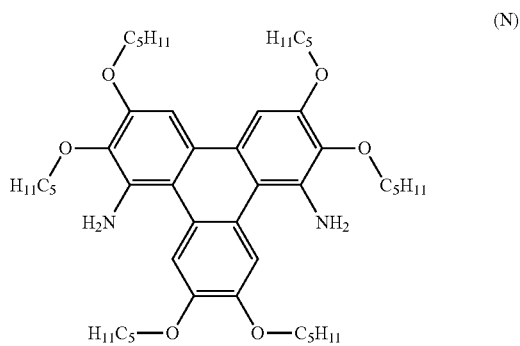

(N)

A yet further aspect of the invention provides a method of synthesising of synthesising polycyclic aromatic hydrocarbon derivatives (P6) comprising the general formula:

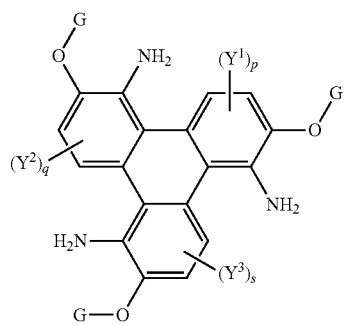

(F6)

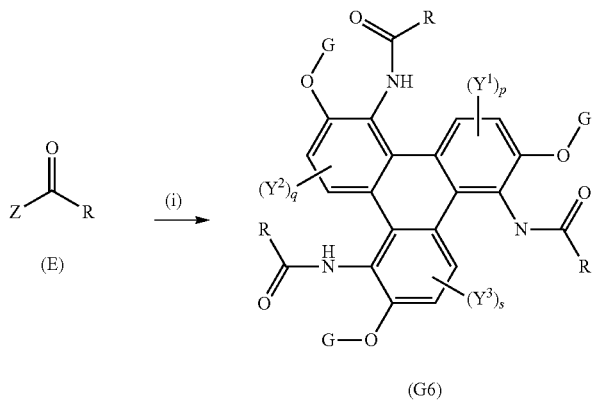

(G6)

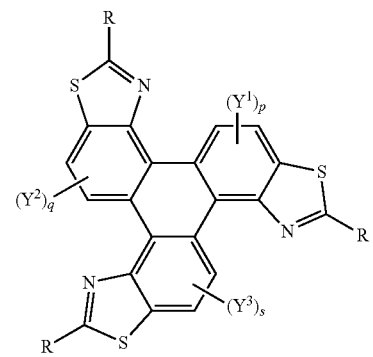

(P6)

wherein (F6) represents a polycyclic aromatic hydrocarbon core, (P6) represents a polycyclic aromatic hydrocarbon derivative;

p, q, and s are independently an integer of 1 to 2;

$Y^1$, $Y^2$, and $Y^3$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;

G independently represents a substituted carbon atom;

(E) represents the reagent;

R independently represents an aromatic group and/or an aliphatic group;

Z is one of an oxygen atom, a derivatised oxygen atom, a chlorine atom, or a bromine atom, or any good leaving group.

The method of synthesising triphenylene derivatives (P7) may comprise the general formula:

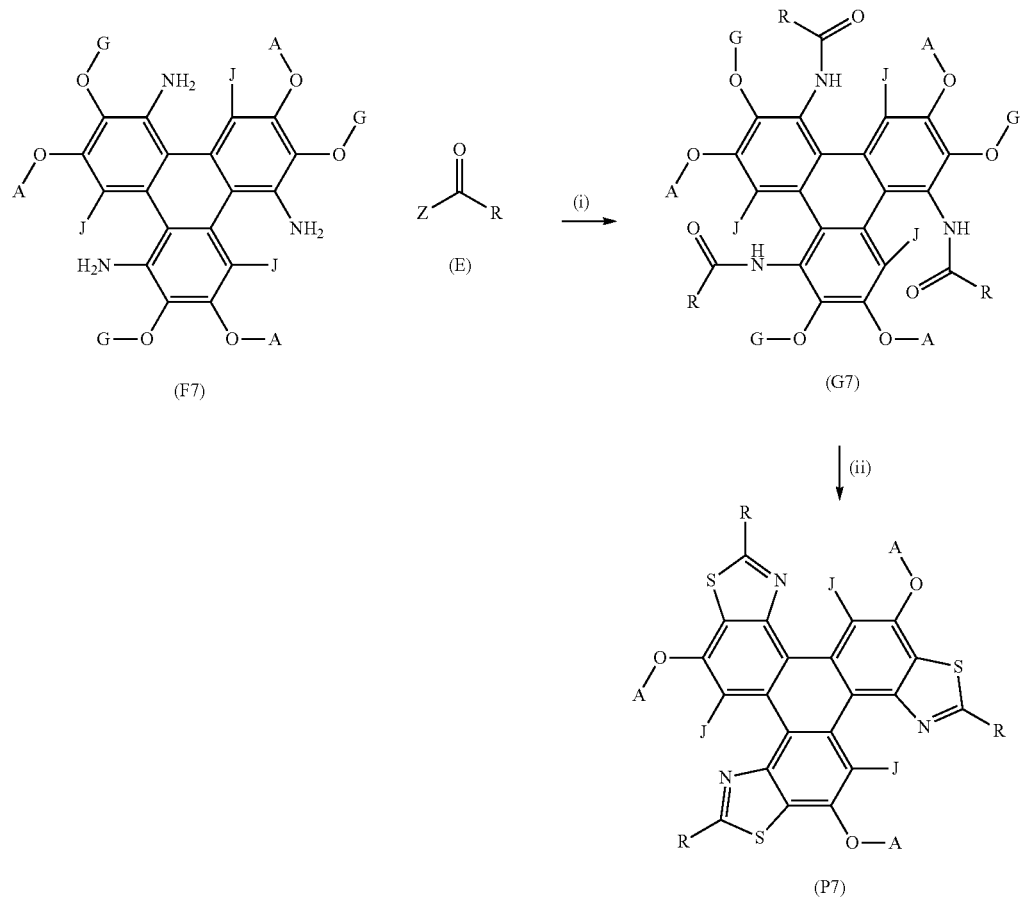

wherein (F7) represents a triphenylene core, (P7) represents a triphenylene derivative;

A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons);

J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

G independently represents a substituted carbon atom;

(E) represents the reagent;

R independently represents an aromatic group and/or an aliphatic group;

Z is one of an oxygen atom, a derivatised oxygen atom, a chlorine atom, or a bromine atom.

(F7) represents the triphenylene core, G is an alkyl or aryl group, (E) represents the reagent, R is an aromatic group and/or an aliphatic group, Z is one of an oxygen atom, e.g. an OH group, a derivatised oxygen atom, a chlorine atom, or a bromine atom, and wherein the triphenylene core (F7) and the reagent (E) undergo Step (i) an intermolecular coupling reaction to produce the triphenylene intermediate (G7). The triphenylene intermediate (G7) may undergo Step (ii) a thionation reaction followed by an intramolecular cyclisation reaction to afford the triphenylene derivatives (P7).

The thionation reaction may be performed using a thionating agent, for example, Lawesson's reagent ammonium phosphorodithioate or thiophosphoryl chloride with triethylamine.

The triphenylene core (F7) of the method of synthesising triphenylene derivatives (P7) may comprise the formula (P):

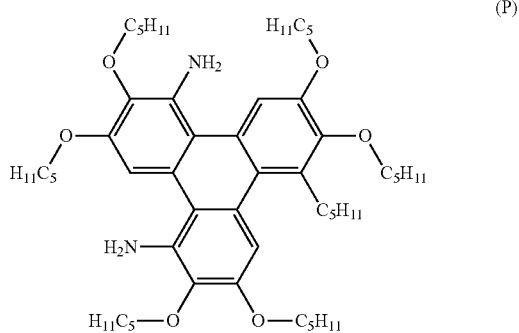

(P)

The method may further comprise a reagent to replace, in situ, group Z with a good leaving group.

The reagent (E) may be a carboxylic acid, for example, benzoic acid or a substituted benzoic acid. The method may further comprise the use of a reagent and/or catalyst to form the triphenylene intermediate, e.g. (J3), from the triphenylene core, e.g. (H3). For example, the reagent may be dicyclohexylcarbodiimide (DCC) or 1-ethyl-3-(3-dimethylaminopropyl)carbodiimide (EDC).

Step (i) of the method may further comprise a species to replace group Z with a good leaving group, for example, the species may be (diacetoxyiodo)benzene).

Alternatively, the reagent (E) may be an acyl chloride, for example, benzyl chloride or a substituted benzyl chloride.

Step (i) of the method may comprise heating the triphenylene core in a solvent, e.g. toluene, wherein Compound (E) is an acyl chloride, i.e. Z is a chlorine atom.

Step (i) and Step (ii) may be performed as separate steps, or may be performed in one single step, in a 'one pot' synthesis.

It is to be understood that the polycyclic aromatic derivatives may be further functionalised to produce analogues. For example, the polycyclic aromatic hydrocarbon derivatives, e.g. the triphenylene derivatives, may undergo bromination, e.g. using $Br_2$, to add a bromine atom to one or more aromatic carbon atoms. The bromine atom may act as a functional group to undergo further chemical transformations, e.g. to functionalise the polycyclic aromatic hydrocarbon derivatives with a phenol group. In embodiments, J may represent a bromine atom and/or a phenol group. The bromine atom and/or phenyl group may be used to further functionalise the polycyclic aromatic hydrocarbon derivative.

Additionally or alternatively, the alkyl groups of one or more of the alkoxy groups (e.g. the $OC_5H_{11}$ groups) may be de-alkylated to form hydroxyl (e.g. phenol) groups (e.g. using boron tribromide).

The polycyclic aromatic hydrocarbon derivatives may act as bio-labels or bio-probes.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. For the avoidance of doubt, the terms "may", "and/or", "e.g.", "for example" and any similar term as used herein should be interpreted as non-limiting such that any feature so-described need not be present. Indeed, any combination of optional features is expressly envisaged without departing from the scope of the invention, whether or not these are expressly claimed. The applicant reserves the right to change any originally filed claim or file any new claim accordingly, including the right to amend any originally filed claim to depend from and/or incorporate any feature of any other claim although not originally claimed in that manner.

Embodiments of the invention will now be described by way of example only with reference to the accompanying drawings in which.

Figure 1:
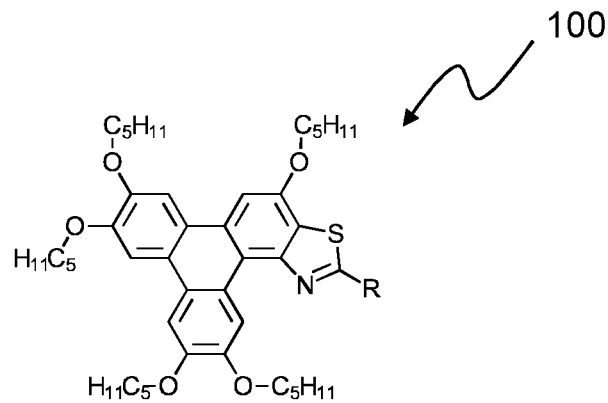
FIG. 1 is a representative structure of a series of triphenylene derivatives according to some embodiments of the invention.

Referring now to FIG. 1, there is shown a representative structure of a triphenylene derivative series 100 according to some embodiments of the invention. In this series, the R group is changed to provide analogues of the triphenylene derivative series 100. The R group may be selected to alter the luminescent and/or other advantageous properties of the triphenylene derivative series 100.

Figure 2:
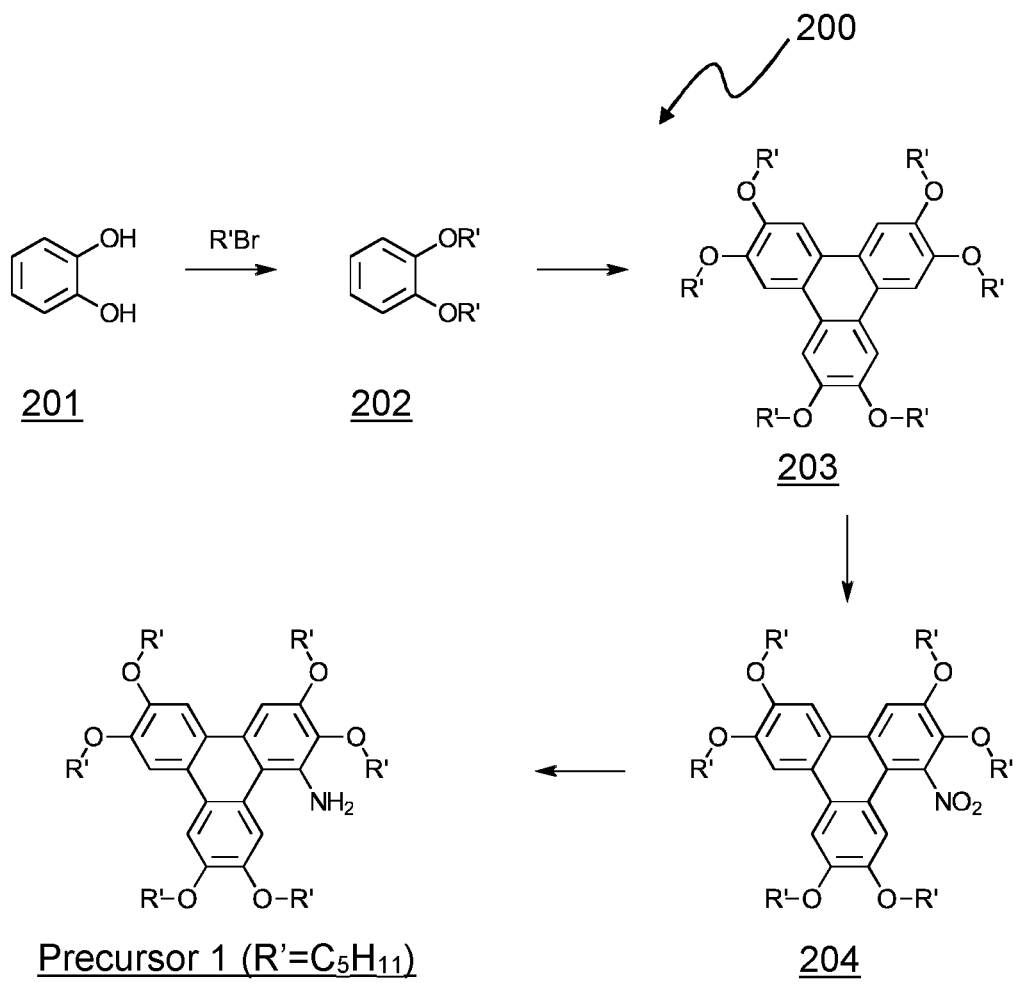
FIG. 2 is a schematic synthetic route of the prior art to the precursors of the triphenylene derivatives according to embodiments of the invention.

Referring now to FIG. 2, there is shown a schematic synthetic route 200 of the prior art (N. Boden et. al. J. Mater. Chem., 1995, 5, 2275) to produce Precursor 1, which is an amine (2,3,6,7,10,11-hexakis(pentyloxy)-1-triphenylenylamine). The full procedures to synthesise Precursor 1, starting from catechol 201, is found in the prior art and are incorporated herein by reference.

Figure 3:
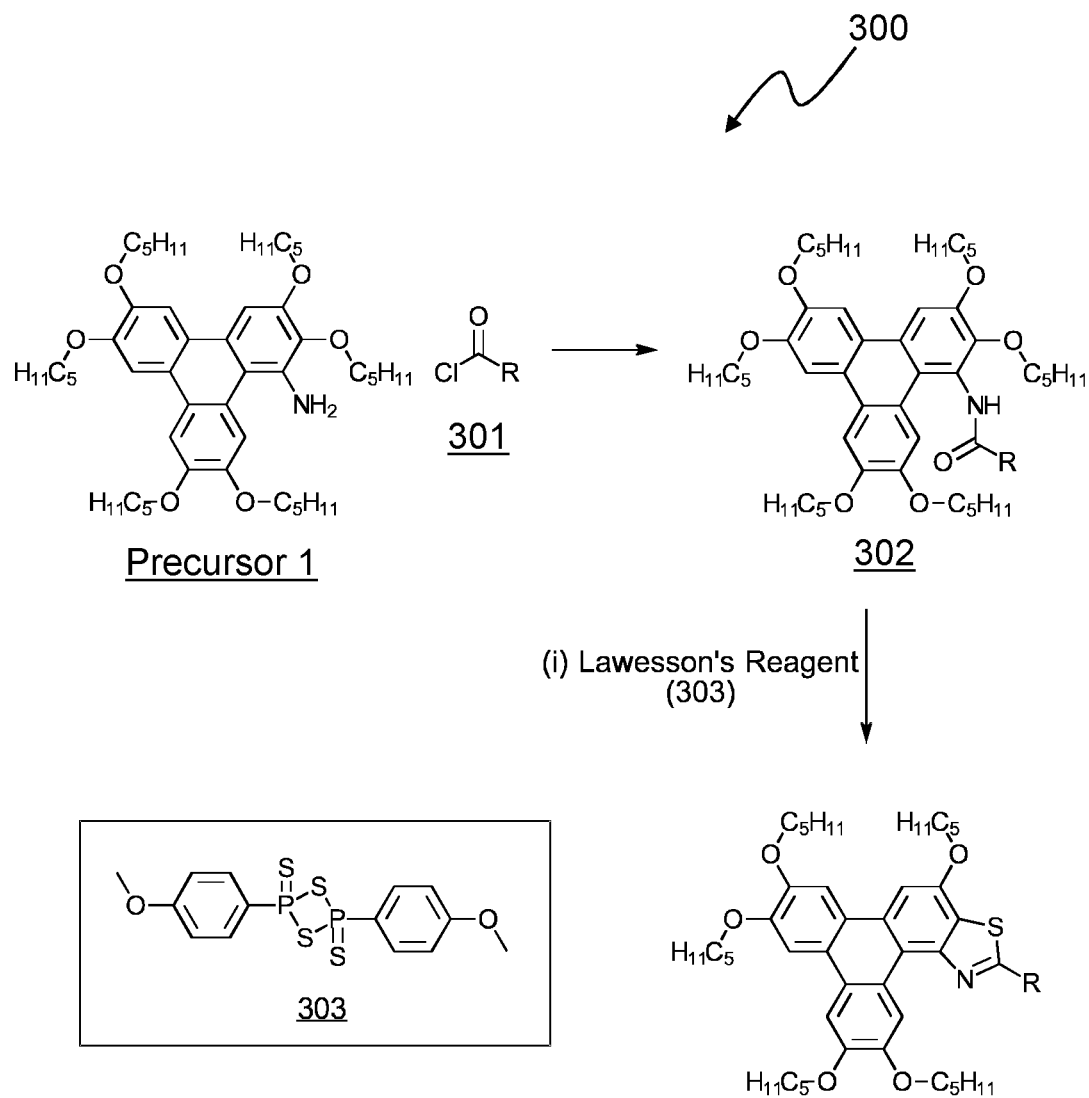
FIG. 3 is a schematic synthetic route for the synthesis of triphenylene derivatives according to embodiments of the invention, as shown in FIG. 1.

Referring now to FIG. 3, there is shown a schematic synthetic route 300 for the formation of the triphenylene derivative series 100 of the present invention. There is shown Precursor 1, an acyl chloride 301, a triphenylene amide intermediate 302, and the triphenylene derivative series 100. The acyl chloride 301 comprises an R group, which is incorporated into the oxazole moiety of the triphenylene derivative series 100. The R group may be an alkyl group, or an aryl group, i.e. the carbon atom bonded to the oxazole moiety in the triphenylene derivative series 100 may be either $sp^2$ or $sp^3$ hybridised.

Advantageously, the method of FIG. 3 enables a huge number of analogues of the triphenylene derivate 100 to be synthesised by varying the R group of the acyl chloride 301 in the method 300. The triphenylene derivative series 100 of the present invention exhibit a number of desirable properties, in particular desirable luminescent characteristics. Advantageously, the R group may be altered to 'tune' these properties. More advantageously, within the known parameters of this invention, the R group may be specifically selected to enable the 'tuning' of the desirable luminescent characteristics. This is demonstrated in detail in the section below.

To further exemplify the invention, reference is also made to the following non-limiting Example.

All compound names were generated using Chem Draw® software.

Figures 4, 5:
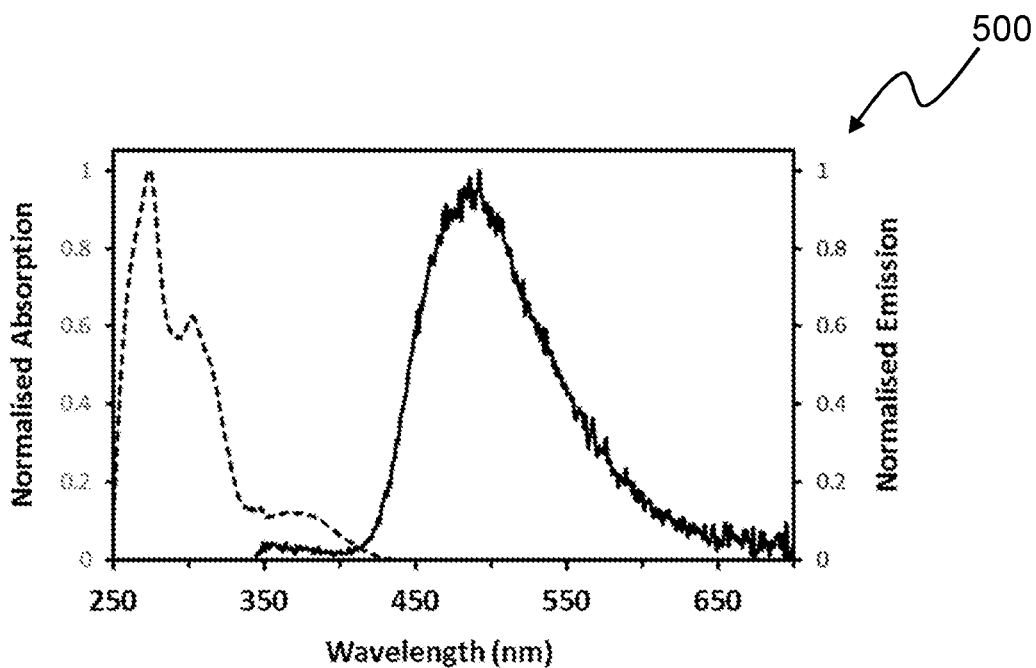
FIG. 4 are examples of triphenylene derivatives according to examples of the invention.
FIG. 5 is an absorption and emission spectra of Compound 1.

Referring to FIG. 4 there is shown Examples (Compound 1) of the triphenylene derivative series 100. The methods for synthesising Compound 1 is described below.

Example 1—Method of Synthesising Compound 1

Compound 1 was synthesised using the following method. A solution of Precursor 1 (100 mg, 0.132 mmol), benzoyl chloride (92 mg, 0.658 mmol) and N,N-diisopropylethylamine (0.1 mL, 0.574 mmol) in PhMe (5 mL) was heated to and held at reflux for 18 h under $N_2$. The reaction was cooled to room temperature and then evaporated to dryness in vacuo purified via flash column chromatography (silica, 60% $CH_2Cl_2$: 40% n-hexane) to afford Compound 302 (R=Ph) as a brown solid (19 mg, 18%).

Compound 302 (R=Ph) had the following characterisation data: $^1H$ NMR δH: (300 MHz, $CDCl_3$) 8.55 (1H, s), 8.45 (1H, s), 8.07 (2H, d, J 7.5), 7.78 (1H, s), 7.74 (1H, s), 7.72 (1H, s), 7.71 (1H, s), 7.59 (1H, d, J 7.0), 7.54 (2H, t, J 7.4), 4.15 (10H, d, J 52.3), 3.67-3.54 (2H, m), 2.00-1.85 (8H, m), 1.70-1.37 (20H, m), 1.34-1.06 (8H, m), 1.02-0.90 (12H, m), 0.83 (3H, t, J 7.0), 0.75 (3H, t, J 7.1) ppm. $^{13}C$ NMR δC: (100 MHz, $CDCl_3$) 174.6, 151.0, 149.7, 148.7, 148.4, 148.4, 144.0, 135.1, 131.7, 130.9, 128.5, 127.9, 126.6, 124.7, 124.2, 123.0, 122.6, 122.0, 110.3, 108.1, 107.7, 106.8, 106.7, 73.4, 70.1, 70.0, 69.5, 69.3, 68.8, 32.1, 30.1, 29.9, 29.6, 29.4, 29.3, 28.7, 28.5, 28.5, 28.1, 22.9, 22.7, 22.6, 14.3, 14.3, 14.1 ppm. MALDI m/z: 863.3 ([M]+100%).

A solution of Compound 302 (R=Ph) (100 mg, 0.116 mmol) and Lawesson's Reagent (175 mg, 0.658 mmol) in PhMe (5 mL) was heated to and held at reflux for 48 h under $N_2$. The reaction was cooled to room temperature and then evaporated to dryness in vacuo. The solid was then heated and held at 240° C. for 15 mins under $N_2$. The crude black solid was then cooled to room temperature and purified via flash column chromatography (silica, 40% $CH_2Cl_2$: 60% n-hexane) to afford Compound 1 as a green solid (17 mg, 19%).

The name for Compound 1 is 2,3,6,11,12-pentakis(pentyloxy)-8-phenyltriphenyleno[1,2-d]thiazole.

Compound 1 had the following characterisation data: $^1H$ NMR δH: (300 MHz, $CDCl_3$) 10.51 (1H, s), 8.24-8.22 (2H, m), 7.92-7.89 (3H, m), 7.76 (1H, s), 7.53-7.52 (3H, m), 4.43-4.26 (10H, m), 2.10-1.95 (10H, m), 1.66-1.57 (10H, m), 1.53-1.47 (10H, m), 1.03-1.00 (15H, m) ppm. $^{13}C$ NMR OC: (100 MHz, $CDCl_3$) 166.4, 152.5, 151.5, 150.2, 149.3, 148.3, 134.7, 130.9, 130.0, 129.3, 127.6, 125.7, 125.4, 124.7, 123.8, 119.0, 112.4, 108.9, 107.2, 106.9, 100.9, 70.3, 70.2, 69.7, 69.2, 69.1, 29.7, 29.6, 29.6, 29.5, 29.4, 28.8, 28.8, 28.8, 23.1, 23.0, 23.0, 23.0 23.0, 14.5, 14.5, 14.5, 14.5 ppm. MALDI m/z: 791.56 ([M]+ 100%).

Example 2—Method of Synthesising Compound 2

Compound 2 was synthesised using the following method. A solution of Precursor 1 (100 mg, 0.132 mmol), 4-cyanobenzoyl chloride (109 mg, 0.658 mmol) and N,N-diisopropylethylamine (0.1 mL, 0.574 mmol) in PhMe (5 mL) was heated to and held at reflux for 18 h under $N_2$. The reaction was cooled to room temperature and then evaporated to dryness in vacuo. The crude brown solid was added to a solution of Lawesson's Reagent (175 mg, 0.658 mmol) in PhMe (5 mL) was heated to and held at reflux for 48 h under $N_2$. The reaction was cooled to room temperature and then evaporated to dryness in vacuo. The solid was then heated and held at 240° C. for 15 mins under $N_2$. The crude black solid was then cooled to room temperature and purified via flash column chromatography (silica, 40% $CH_2Cl_2$: 60% n-hexane) to afford Compound 2 as a yellow solid (5 mg, 5%).

The name for Compound 2 is 4-(2,3,6,11,12-pentakis(pentyloxy)triphenyleno[1,2-d]thiazol-8-yl)benzonitrile.

Compound 2 had the following characterisation data: $^1H$ NMR δH: (300 MHz, $CDCl_3$) 10.38 (1H, s), 8.31 (2H, d, J 8.4), 7.97-7.88 (4H, m), 7.79 (1H, d, J 8.5), 4.41-4.26 (10H, m), 2.06-1.95 (10H, m), 1.61-1.55 (10H, m), 1.51-1.44 (10H, m), 1.03-0.97 (15H, m) ppm. MALDI m/z: 816.9 ([M]+90%), 817.9 ([M+H]+ 100%).

Properties of Triphenylene Derivative Series 100

The triphenylene derivative series 100 of the present invention exhibits a number of advantageous properties that are useful in many applications. Some of these advantageous properties are demonstrated and described below in a non-limiting way.

Referring now to FIG. 5, there is shown an absorption and emission spectra 500 of Compound 1. Compound 1 was dissolved in ethyl acetate, and the absorption and emission was measured. The absorption maxima was shown to be 274 nm, and the emission maxima was shown to be 492 nm.

Figure 6:
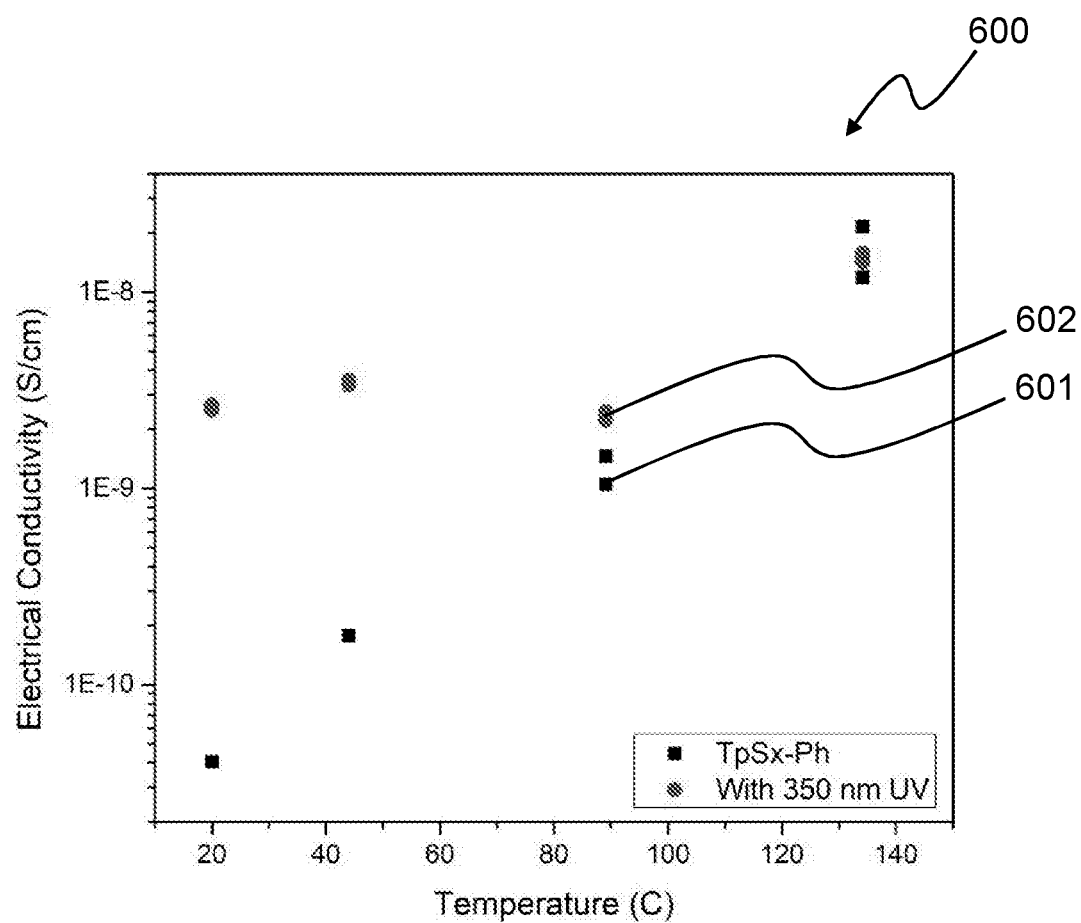
FIG. 6 is a graph showing electrical conductivity and photoconductivity data for Compound 1.

FIG. 6 is a graph 600 showing electrical conductivity and photoconductivity data for Compound 1. The electrical conductivity 601 was measured at different temperatures for Compound 1. The photoconductivity 602 was measured at different temperatures for Compound 1 whilst irradiating with UV light at 350 nm.

Large Stokes Shift

It should be noted that by Stokes shift, we also mean a 'pseudo' Stokes shift. The IUPAC definition of the Stokes shift requires that the difference in the band maxima of the absorption and luminescence arise from the same electronic transition. However, it is widely referred to in the literature in general terms to mean the difference in excitation and emission wavelengths, regardless of electronic transition.

Emission Across the Entire Visible Spectrum, which Varies with R Group Structure Advantageously, the emission spectra of the compounds of the invention span a large portion of the visible spectrum. The R group need not be limited to those disclosed, and may be any alkyl or aryl group. In particular, variation of the R group with, for example, a different aromatic hydrocarbon group has been shown to result in a shift in the emission spectra. The shift in emission, and consequently the resulting visible colour of a specific triphenylene derivative, within the triphenylene derivative series 100, may be predicted with a good level of certainty for variation of the R group. Advantageously, this provides a huge number of analogues, for example wherein R is an aryl group, so that the emission is a colour within the visible spectrum, and this visible colour may be 'tuned' by slight structural alteration to the R group of the triphenylene derivative series 100 of the present invention.

Application of Triphenylene Derivative Series 100 in Electroluminescent Devices

The triphenylene derivatives of the present invention may also be used in a functional layer of an OLED (Organic Light Emitting Diode). It has been shown that the triphenylene derivatives of the present invention may exhibit excellent emitting, charge transporting, and/or charge blocking abilities.

Figure 7:
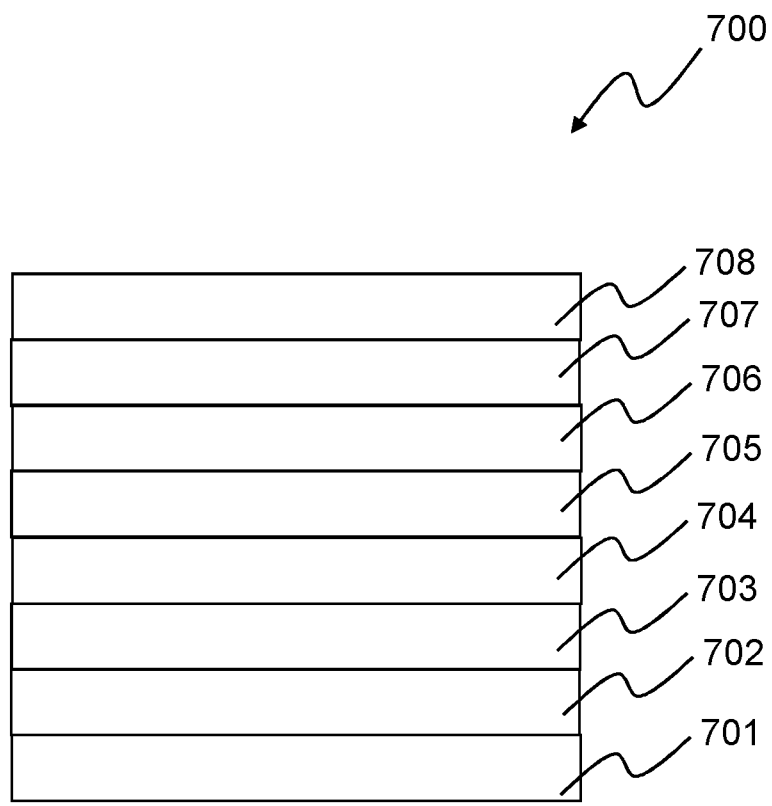
FIG. 7 is an OLED according to a further aspect of the invention.

Referring now to FIG. 7 there is shown an OLED 700. The OLED 700 comprises the following successive layers: a substrate 701, an anode 702, an optional hole transport layer 703, an optional electron blocking layer 704, an emissive layer 705, an optional hole blocking layer 706, an optional electron transport layer 707, and a cathode 708.

Each layer described above may comprise any suitable material known to those skilled in the art, and may comprise more than one type of material or layer. For example, the substrate 701 may comprise glass, quartz, polymers, and so on. The thickness is not critical and may be, for example, between 25 to 1000 microns depending on the application of the device. The anode 702 may comprise any electrically conductive material, e.g. metal, or a conductive metal oxide such as ITO (indium tin oxide). The hole transport layer 703 may comprise, for example, 1,4-bis[(1-naphthyphenyl)-amino]biphenyl (NPD). The emissive layer 705 may comprise aluminium tris(8-hydroxyquinoline). The hole blocking layer 706 may comprise 2,9-dimethyl-4,7-diphenyl-1,10-phenanthroline (bathocuproine, BCP). The electron transport layer 707 may comprise, for example, metal chelates such as, for example, aluminium tris(8-hydroxyquinoline). The cathode 708 may comprise any metal, for example, aluminium, lithium, magnesium, and/or calcium.

The emissive layer 705 comprises the triphenylene derivatives of the present invention, e.g. the triphenylene derivative series 100.

The OLED 700 is fabricated in the following manner:
The anode 702 is patterned upon the clean substrate 701.
The substrate 701, which is patterned with the anode 702, is treated with oxygen for 1 to 5 minutes.
The substrate 701, which is patterned with the anode 702, is placed in a thermal evaporator and the pressure is reduced to below $6 \times 10^{-6}$ torr.
The hole transport layer 703, the electron blocking layer 704, the emissive layer 705, the hole blocking layer 706, the electron transport layer 707, and the cathode 708 are successively formed in the listed order by thermal evaporation.

It will be appreciated by those skilled in the art that several variations to the aforementioned embodiments are envisaged without departing from the scope of the invention. For example, the R group of the triphenylene derivative series 100 and Precursor 1 need not be restricted to $C_5H_{11}$, and may be any stable alkyl or aryl group capable of alkylating the phenol moiety of the triphenylene moiety.

Advantageously, the triphenylene derivative series 100 of the present invention may be further functionalised, for example, by derivatisation of functional groups within the R group. This provides the possibility of using the triphenylene derivative of the present invention as biotags or probes, for example.

It will also be appreciated by those skilled in the art that any number of combinations of the aforementioned features and/or those shown in the appended drawings provide clear advantages over the prior art and are therefore within the scope of the invention described herein.

The invention claimed is:

1. Polycyclic aromatic hydrocarbon derivatives, represented by the following general formula:

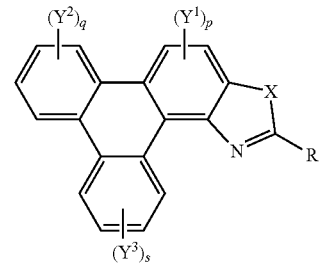

wherein X is one of phosphorus, arsenic, antimony, bismuth, sulphur, selenium or tellurium;
R independently represents an aromatic group or an aliphatic group;
p is an integer of 1 to 2;
q and s are independently integers of 1 to 4;
$Y^1$, $Y^2$, and $Y^3$ independently represent a hydrogen atom, a deuterium atom, a fluorine atom, a chlorine atom, a bromine atom, a carbon atom, an OH, a carboxylic acid group, a glycol, an alkoxy, a thioalkoxy, an amino, an acetate, an amide, a thioamide, a thioester, an azo, a silyl group, an alkylated nitrogen atom, a cyano group, a nitro group, a branched or straight chain alkyl group which may be further functionalized and/or an aryl group which may be further functionalized.

2. Polycyclic aromatic hydrocarbon derivatives, wherein the polycyclic aromatic hydrocarbon derivatives are triphenylene derivatives represented by the following general formula:

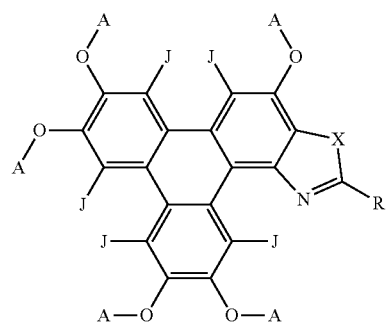

wherein X is one of phosphorus, arsenic, antimony, bismuth, sulphur, selenium or tellurium;
R independently represents an aromatic group or an aliphatic group;
A independently represents a hydrogen atom, an aryl group, an alkyl group comprising 1 to 20 carbons or an alkyl ether;
J independently represent a hydrogen atom, a deuterium atom, a fluorine atom, a chlorine atom, a bromine atom, a carbon atom, an OH, an alkylated oxygen atom, a carboxylic acid group, a glycol, an alkoxy, a thioalkoxy, an amino, an acetate, an amide, a thioamide, a thioester, an azo, a silyl group, an alkylated nitrogen atom, a cyano group, a nitro group, a branched or straight chain alkyl group which may be further functionalized or an aryl group which may be further functionalized.

3. Polycyclic aromatic hydrocarbon derivatives, wherein the polycyclic aromatic hydrocarbon derivatives are triphenylene derivatives represented by the following general formula:

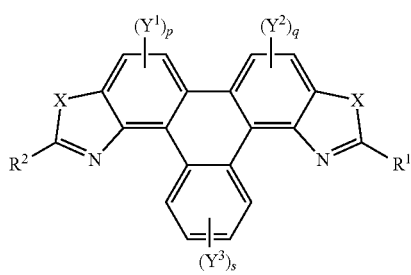

wherein X is independently one of phosphorus, arsenic, antimony, bismuth, sulphur, selenium or tellurium;
$R^1$ and $R^2$ independently represents an aromatic group or an aliphatic group;
p and q are independently an integer of 1 to 2;
s is an integer of 1 to 4;
$Y^1$, $Y^2$, and $Y^3$ independently represent a hydrogen atom, a deuterium atom, a fluorine atom, a chlorine atom, a bromine atom, a carbon atom, an OH, a carboxylic acid group, a glycol, an alkoxy, a thioalkoxy, an amino, an acetate, an amide, a thioamide, a thioester, an azo, a silyl group, an alkylated nitrogen atom, a cyano group, a nitro group, a branched or straight chain alkyl group which may be further functionalized and/or an aryl group which may be further functionalized.

4. Polycyclic aromatic hydrocarbon derivatives, wherein the polycyclic aromatic hydrocarbon derivatives are triphenylene derivatives represented by the following general formula:

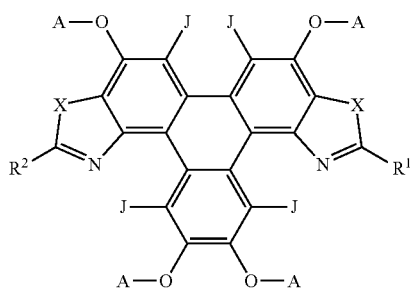

wherein X is independently one of phosphorus, arsenic, antimony, bismuth, sulphur, selenium or tellurium;
$R^1$ and $R^2$ independently represents an aromatic group or an aliphatic group;
A independently represents a hydrogen atom, an aryl group, an alkyl group comprising 1 to 20 carbons or an alkyl ether;
J independently represent a hydrogen atom, a deuterium atom, a fluorine atom, a chlorine atom, a bromine atom, a carbon atom, an OH, an alkylated oxygen atom, a carboxylic acid group, a glycol, an alkoxy, a thioalkoxy, an amino, an acetate, an amide, a thioamide, a thioester, an azo, a silyl group, an alkylated nitrogen atom, a cyano group, a nitro group, a branched or straight chain alkyl group which may be further functionalized or an aryl group which may be further functionalized.

5. Polycyclic aromatic hydrocarbon derivatives represented by the following general formula:

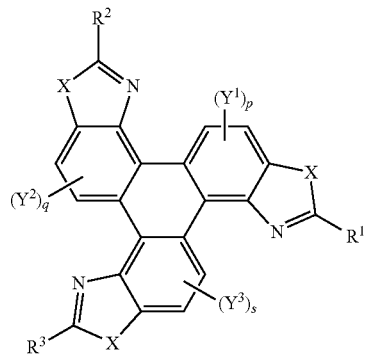

wherein X is independently one of phosphorus, arsenic, antimony, bismuth, sulphur, selenium or tellurium;
$R^1$, $R^2$, $R^3$ independently represent an aromatic group or an aliphatic group;
p, q, and s are each independently an integer of 1 to 2;
$Y^1$, $Y^2$, and $Y^3$ independently represent a hydrogen atom, a deuterium atom, a fluorine atom, a chlorine atom, a bromine atom, a carbon atom, an OH, an alkylated oxygen atom, a carboxylic acid group, a glycol, an alkoxy, a thioalkoxy, an amino, an acetate, an amide, a thioamide, a thioester, an azo, a silyl group, an alkylated nitrogen atom, a cyano group, a nitro group, a branched or straight chain alkyl group which may be further functionalized and/or an aryl group which may be further functionalized.

6. Polycyclic aromatic hydrocarbon derivatives, wherein the polycyclic aromatic hydrocarbon derivatives are triphenylene derivatives and represented by the following general formula:

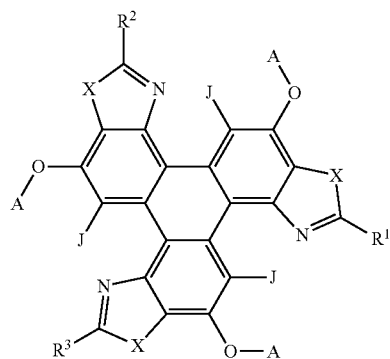

wherein X is independently one of phosphorus, arsenic, antimony, bismuth, sulphur, selenium or tellurium;
$R^1$, $R^2$, $R^3$ independently represent an aromatic group or an aliphatic group;
A independently represents a hydrogen atom, an aryl group, an alkyl group comprising 1 to 20 carbons or an alkyl ether;

J independently represent a hydrogen atom, a deuterium atom, a fluorine atom, a chlorine atom, a bromine atom, a carbon atom, an OH, an alkylated oxygen atom, a carboxylic acid group, a glycol, an alkoxy, a thioalkoxy, an amino, an acetate, an amide, a thioamide, a thioester, an azo, a silyl group, an alkylated nitrogen atom, a cyano group, a nitro group, a branched or straight chain alkyl group which may be further functionalized or an aryl group which may be further functionalized.

7. The polycyclic aromatic hydrocarbon derivatives according to claim 1, wherein X is a sulphur atom.

8. The polycyclic aromatic hydrocarbon derivatives according to claim 1, wherein R comprises a phenyl group.

9. The polycyclic aromatic hydrocarbon derivatives according to claim 1, wherein R comprises a heterocyclic group.

10. The polycyclic aromatic hydrocarbon derivatives according to claim 1, wherein R comprise a polycyclic aromatic hydrocarbon.

11. The polycyclic aromatic hydrocarbon derivatives according to claim 10, wherein R comprise one of naphthalene, anthracene, or pyrene.

12. The polycyclic aromatic hydrocarbon derivatives according to claim 1 selected from the structures Compound 1 and Compound 2:

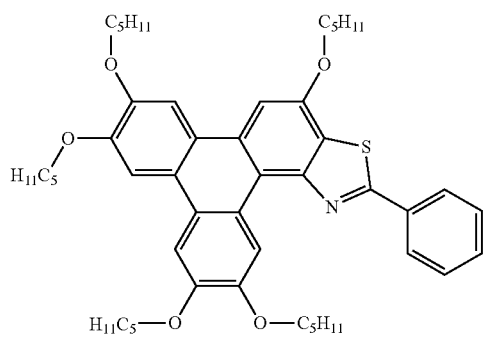

Compound 1:

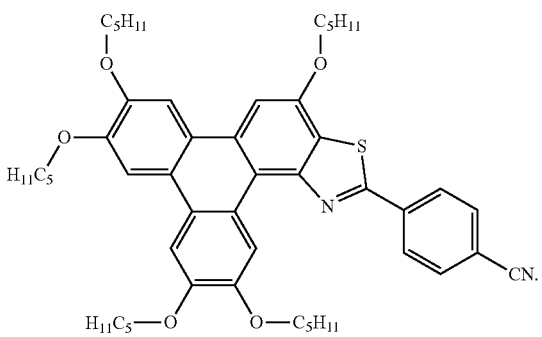

Compound 2:

13. A device comprising the polycyclic aromatic hydrocarbon derivatives according to claim 1.

14. A device according to claim 13, wherein the device is an organic electroluminescent device, an OPV (organic photovoltaic) device, a thin-film transistor, or a liquid crystal display.

15. A device of claim 14, wherein the organic electroluminescent device comprises a pair of electrodes and one or more layers interposed therebetween, wherein the one or more layers comprise one or more of the polycyclic aromatic hydrocarbon derivatives.

16. A device of claim 13, wherein the polycyclic aromatic hydrocarbon derivatives exhibit a Stokes shift of between 200 $cm^{-1}$ to 36,000 $cm^{-1}$ when dissolved in ethyl acetate and measured at ambient temperature.

17. A device of claim 13, wherein the polycyclic aromatic hydrocarbon derivatives exhibit a conductivity value of $5.0 \times 10^{-13}$ S $cm^{-1}$ and $1 \times 10^{2}$ S $cm^{-1}$.

* * * * *